United States Patent [19]

Rees, Jr.

[11] Patent Number: 5,583,205

[45] Date of Patent: Dec. 10, 1996

[54] METALORGANIC CHEMICAL VAPOR DEPOSITION METHOD FOR DEPOSITING F-SERIES METAL OR NITROGEN AND METAL AMIDES FOR USE IN MOCVD

[75] Inventor: William S. Rees, Jr., Lithonia, Ga.

[73] Assignee: Florida State University, Tallahassee, Fla.

[21] Appl. No.: 151,500

[22] Filed: Nov. 12, 1993

[51] Int. Cl.$^6$ ............... C07F 5/00; B05D 5/12; C23C 16/00
[52] U.S. Cl. ............ 534/15; 427/124; 427/248.1
[58] Field of Search .............. 534/15; 427/124, 427/248.1

[56] References Cited

FOREIGN PATENT DOCUMENTS

| 563557 | 2/1993 | European Pat. Off. ........ C07C 43/13 |
| A563557 | 10/1993 | European Pat. Off. . |

OTHER PUBLICATIONS

CA113:172252, 1990.
CA110:95441, 1988.
Derwent World Patent Index (WPI) abstract corresponding to EP–A–563557, WPI Acc. No. 93–312997/40, 1993.
Bradley et al., "Low Co–ordination Numbers in Lanthanide and Actinide Compounds. Part 1. The Preparation and Characterization of Tris{bis(trimethylsilyl)–amido}lanthanides", Journal of the Chemical Society (London), Dalton Transactions–Inorganic Chemistry pp. 1021–1023 (1973).
Lappert et al., "Amides of Zinc, Cadium, and Mercury: Synthesis, Physical Properties, and Structures", Metal and Metalloid Amides, Chapter 9, pp. 545–566 (1980).
Shustov et al., "Synthesis and Some Properties of Phenylethynyl Derivatives of Trivalent Lanthanides", Metalloorganicheskaya Khimiya, vol. 3, pp. 624–628 (1990).
Power et al. "Synthesis and Characterization of the Isoelectronic $d^{10}$ Species $[Cu\{N(SiMePh_2)_2\}_2]$–and $Zn\{N(SiMePh_2)_2\}_2$", Inorganic Chemistry, vol. 30, pp. 5013–5015 (1991).
Rees et al., "Sythesis and X–ray Diffraction Crystal Structure of $Zn\{N[(C(CH_3)_3)\ (Si(CH_3)_3)]\}_2$, The First Solid–State Characterization of Homoleptic Zinc Amide", Polyhedron, vo. 11, No. 13, pp. 1697–1699 (1992).
Rees et al., "OMVPE Growth of ZnSe Utilizing Zinc Amides as Source Compounds: Relevance to the Production of p–Type Material" Material Research Society Symposium Proceedings, vol. 242, pp. 281–286 (1992).
Rees et al., "Synthesis, Characterization and Evaluation of Zinc–Amides as Potential Dopant Sources for ZnSe OMVPE", Material Research Society Symposium Proceedings, vol. 282, pp. 63–67 (1993).
La Duca et al., "Preparation of Lanthanide Nitrides via Ammonolysis of Molten $\{(Me_3Si)_2N\}_3Ln$: Onset of Crystallization Catalyzed by $LinH_2$ and LiCl", Inorganic Chemistry, vol. 31, No. 8, pp. 1311–1313 (1992).
Greenwald et al., "MOCVD Erbium Sources", published in Materials Research Society Symposium Proceedings (1993).
Greenwald et al., "MOCVD Erbium Sources", presented in San Francisco, CA, Apr., 1993.
Spear et al., "Chemical Vapor Deposition in the 21st Century" pp. 39–47 (1993).
W. S. Rees, Jr. et al., "Evaluation of $Zn\{N[Si(CH_3)_3]_2\}_2$ as a p–type Dopant in OMVPE Growth of ZnSe", Journal of Electronic Materials, vol. 21, 1992.

*Primary Examiner*—Shean C. Wu
*Attorney, Agent, or Firm*—Senniger, Powers, Leavitt & Roedel

[57] ABSTRACT

A metalorganic chemical vapor deposition (MOCVD) method for depositing an F-series metal onto a semiconductor or other substrate or for incorporating nitrogen as a p-type dopant in Group II–VI semiconductor materials. The MOCVD method utilizes an F-series metal amide or zinc amide composition as the source compound for the F-series metal or nitrogen, respectively. Novel erbium amide and zinc amide compositions are disclosed along with methods for preparing the metal amide compositions.

4 Claims, 2 Drawing Sheets

METALORGANIC CHEMICAL VAPOR DEPOSITION METHOD FOR DEPOSITING F-SERIES METAL OR NITROGEN AND METAL AMIDES FOR USE IN MOCVD

The U.S. Government has rights in this invention pursuant to Contract No. F49620-92-C-0060 awarded by Ballistic Missile Defense Organization (BMDO).

BACKGROUND OF THE INVENTION

The present invention relates to a metalorganic chemical vapor deposition method for depositing an F-series metal (i.e., elements having an atomic number of 57 through 71 and 89 through 103) onto a semiconductor or other substrate, a metalorganic chemical vapor deposition method for incorporating nitrogen as a p-type dopant in Group II–VI semiconductor materials, metal amide compositions which can be used in metalorganic chemical vapor deposition as the source compound for an F-series metal or nitrogen, and to methods for preparing the metal amide compositions.

Generally, chemical vapor deposition (CVD) involves producing a reactant gas by contacting a volatile source compound for the material to be grown with a carrier gas. The reactant gas is introduced into a heated reactor chamber of an epitaxial reactor system that contains a substrate supported by a susceptor. Upon thermal decomposition of the source compound contained in the reactant gas, the desired component of the reactant gas is condensed from the vapor phase and grows epitaxially on the substrate. When a metalorganic composition is used as a source compound in CVD, the method is properly called organometallic vapor phase epitaxy (OMVPE) or metalorganic chemical vapor deposition (MOCVD). CVD offers several advantages over competing epitaxy methods such as molecular beam epitaxy (MBE), including: (1) the ability to grow relatively large surface area materials; (2) higher throughput and (3) lower equipment costs.

MOCVD is widely used for the epitaxial growth of semiconductor materials used in the electronics industry. A common disadvantage of semiconductor materials is a temperature dependent energy gap between the electron valence and conduction bands. This drawback limits the performance of electroluminescent and optoelectronic semiconductor components which utilize the energy released upon transition of a promoted electron from the conduction band to a "hole" in the valence band (e.g., LED's, diode lasers, etc.). One solution to this problem is to incorporate a dopant into the semiconductor material which provides a pathway for election transitions from the conduction band to lower energy states that subsequently produces an essentially temperature independent energy emission. In order to serve as an effective dopant for this purpose, an element must have electron orbital transitions within the appropriate energy range for the semiconductor material and should be essentially free of competing energy transitions.

F-series metals have accessible f—f electron orbital transitions which fall within the appropriate energy range for a variety of semiconductor materials, including Group III–V (e.g., GaAs, AlGaAs); Group II–VI (e.g., ZnSe, CdS); and Group IV (e.g., Si, SiC, SiGe) semiconductors. Thus, F-series metals are suitable dopants to incorporate in these various semiconductor materials to reduce the effects of a temperature dependent band gap on semiconductor performance. "Rare Earth Doped Semiconductors", Symposium held April 13–15, 1993, San Francisco, Calif., *Materials Research Society Symposium Proceedings*, Vol. 301 (1993). Diode lasers made from stable, erbium-doped GaAs and AlGaAs are of particular importance because their 1538 nm wavelength matches that needed for efficient pumping of erbium-doped fibers used in optical amplifiers.

Group II–VI semiconductor materials such as zinc selenide (ZnSe) and cadmium sulfide (CdS) which contain a p-n junction may be used in optoelectronic devices that function in the blue region of the visible spectrum such as blue lasers, blue LED's and blue emission devices both active and passive. However, introducing p-type dopants into the Group II–VI lattice system has proven to be problematic. Marginal success has been achieved incorporating lithium as a p-type dopant at the Zn lattice site of ZnSe grown by MOCVD using $Zn(CH_3)_2$ and $Se(CH_3)_2$ as the Group II–VI element source compounds and tertiary-butyllithium or cyclopentadienyl lithium as the lithium source compound. Also, bis-bis-(trimethylsilyl) zinc amide has been used in MOCVD as a nitrogen source compound in depositing a nitrogen-doped ZnSe epitaxial layer using $Zn(C_2H_5)_2$ and $H_2Se$ as the Group II–VI element source compounds. Rees et al. "Evaluation of Zn $\{N[Si(CH_3)_3]_2\}_2$ as a p-type Dopant in OMVPE Growth of ZnSe", *Journal of Electronic Materials*, Vol. 21 No. 6, pp. 361–366, (1992). Although bis-bis-(trimethylsilyl) zinc amide proved to be an adequate source compound for nitrogen doping of ZnSe, the effectiveness of the MOCVD process could be improved by utilizing a nitrogen source compound exhibiting a more consistent vapor pressure and cleaner decomposition kinetics so that fewer contaminants are left behind. Furthermore bis-bis-(trimethylsilyl) zinc amide can be difficult to purify for use in MOCVD and may be unstable at some MOCVD operating conditions.

SUMMARY OF THE INVENTION

Among the objects of the present invention, therefore, is the provision of an MOCVD method for depositing an F-series metal onto a semiconductor or other substrate; the provision of erbium amide compositions for use as erbium source compounds in MOCVD to deposit erbium; the provision of a method for preparing F-series metal amide compositions in high yield; the provision of an MOCVD method for incorporating nitrogen as a p-type dopant into Group II–VI semiconductor materials; the provision of zinc amide compositions for use as nitrogen source compounds in MOCVD to deposit nitrogen.

Briefly, the present invention is directed to an MOCVD method for depositing an F-series metal onto a substrate. The method comprises introducing a reactant gas into the reactor chamber of an epitaxial reactor system. The reactant gas comprises an F-series metal amide having a vapor pressure of at least $1 \times 10^{-5}$ torr at 100° C. The F-series metal of the amide is ligated to at least one amide ligand having the formula wherein $R_1$ and $R_2$ are independently alkyl, alkenyl, aryl or di- or trialkyl-substituted silyl, or together with the nitrogen atom to which they are attached comprise a heterocyclic ring. The F-series metal amide is then decomposed to deposit the F-series metal onto the substrate.

The invention is further directed to erbium amide compositions for use as erbium source compounds in MOCVD. The erbium amide compositions have a vapor pressure of at least $1 \times 10^{-5}$ torr at 100° C. and have the formula wherein $R_1$ and $R_2$ are independently alkyl, alkenyl, aryl or di- or trialkyl-substituted silyl, or together with the nitrogen atom to which they are attached comprise a heterocyclic ring, Q is a monodentate or oligodentate ligand other than an amide ligand, x is an integer $\geq 1$, and y is an integer $\geq 0$, such that the F-series metal is substantially inert to further ligation.

The invention is further directed to a method of preparing F-series metal amides by the metathesis reaction between an F-series metal halide and a solution of an alkali metal amide. The method is characterized in that portions of the F-series metal halide are added to the alkali metal amide to form the F-series metal amide.

The invention is further directed to an MOCVD method for incorporating nitrogen as a p-type dopant into ZnSe or CdS semiconductor material. The method comprises introducing a reactant gas into the reactor chamber of an epitaxial reactor system. The reactant gas contains a zinc amide having a vapor pressure of at least $1 \times 10^{-5}$ torr at 200 ° C. and having the formula wherein $R_1$, $R_2$, $R'_1$ and $R'_2$ are independently alkyl, alkenyl, aryl, or di- or trialkyl-substituted silyl, or together with the nitrogen atom to which they are attached comprise a heterocyclic ring, provided that if $R_1$, $R_2$, $R'_1$ and $R'_2$ are each trialkyl-substituted silyl, at least one of $R_1$, $R_2$, $R'_1$ or $R'_2$ have at least one alkyl group containing a βhydrogen. The zinc amide is then decomposed to deposit nitrogen onto the substrate.

The invention is further directed to zinc amide compositions for use as nitrogen source compounds in MOCVD to deposit nitrogen. The zinc amide compositions have a vapor pressure of at least $1 \times 10^{-5}$ torr at 200 ° C. and have the formula wherein $R_1$, $R_2$, $R'_1$ and $R'_2$ are independently alkyl, alkenyl, aryl, or di- or trialkyl-substituted silyl, or together with the nitrogen atom to which they are attached comprise a heterocyclic ring, provided that if $R_1$, $R_2$, $R'_1$ and $R'_2$ are each trialkyl-substituted silyl, at least one of $R_1$, $R_2$, $R'_1$ or $R'_2$ have at least one alkyl group containing a β hydrogen.

Other objects and features of this invention will be in part apparent and in part pointed out hereinafter.

DETAILED DESCRIPTION OF THE PREFERRED EMBODIMENTS

As used herein, X means halide; iPr means isopropyl; nPr means n-propyl; nBu means nbutyl; tBu means tertbutyl; Cyhex means cyclohexyl; Ph means phenyl; DMS means dimethylsilyl; and TMS means trimethylsilyl; "interacting with" shall mean covalent bonding, ionic bonding or electrostatic attraction; and alkyl shall mean both straight-chain and cycloalkyl.

In accordance with the present invention, an MOCVD method is used to deposit an epitaxial layer of an F-series metal onto a substrate. This MOCVD method can be used, thus, to prepare Group III–V, Group II–VI or Group IV semiconductor materials doped with an F-series metal for use in optoelectronic or electroluminescent components such as diode lasers or LED's. Alternatively, the epitaxial layer can be used as an oxidation barrier coating, wear-resistant coating, catalyst structure as well as to provide a substantially pure source of the F-series metal. The present invention is also directed to an MOCVD method for incorporating nitrogen as a p-type dopant in ZnSe or CdS. ZnSe and CdS semiconductor material doped with nitrogen can be used, for example, in optoelectronic devices which function in the blue region of the visible spectrum and blue emission devices both active and passive.

In the MOCVD method of the present invention for depositing an F-series metal, the source compound for the F-series metal is an F-series metal amide. The F-series metal amides are substantially inert toward further ligation and have a vapor pressure of at least about $1 \times 10^{-5}$ torr at 100° C., preferably, at least about 0.1 torr at 100° C., and more preferably at least about 1 torr at 100° C. The metal of the F-series metal amide is ligated to at least one amide ligand having the formula wherein $R_1$ and $R_2$ are independently alkyl, alkenyl, aryl or dior trialkyl-substituted silyl. Preferably, $R_1$ and $R_2$ are $C_1$–$C_6$ alkyl such as n-propyl, isopropyl, tertbutyl, isobutyl, cyclopropyl or cyclohexyl or di- or trialkyl-substituted silyl such as dimethylsilyl, trimethylsilyl or triethylsilyl. Furthermore, at least one of $R_1$ and $R_2$ is preferably di- or trialkyl-substituted silyl. Optionally, $R_1$ and $R_2$ and the nitrogen atom to which they are attached may together form a heterocyclic ring structure such as that found in pyrazole, carbazole or indole. In addition to nitrogen and carbon, the heterocyclic ring may additionally comprise silicon. Preferably, the F-series metal of the amide is non-radioactive.

In general, the F-series metal amides correspond to the formula wherein M is the F-series metal, $R_1$ and $R_2$ are as defined above, Q is a monodentate or oligodentate ligand other than an amide ligand, x is an integer greater than or equal to 1 and y is an integer greater than or equal to 0. If x is $\geq 2$, $R_1$ and $R_2$ of each amide ligand is independently alkyl, alkenyl, aryl or di- or trialkyl-substituted silyl and is selected without regard to other amide ligands. For example, if x=2 and y=0, the metal amide may have the following formula wherein $R_1$ is selected independent of $R_2$, $R'_1$ and $R'_2$. Extending this example, therefore, $R_1$ may be trimethylsilyl, $R'_1$ may be isopropyl, $R_2$ may be tertbutyl, and $R'_2$ may be cyclohexyl. Alternatively, each of the substituents of the F-series metal amide may be trimethylsilyl. Thus, the F-series metal amides may be heteroleptic or homoleptic.

If $y \geq 1$, the non-amide, monodentate or oligodentate ligand(s), Q, may be virtually any ligand known to those of ordinary skill, provided the metal amide is substantially inert to further ligation. Thus the non-amide ligand(s) may be neutral or ionic. Such ligands may be selected, for example, from ethylene diamine, ethylene glycol dimethyl ether, cyclopentadienyls, alkoxides, thiolates, β-diketonates, phosphides, halides and hydrides. Furthermore, if y is $\geq 2$, each non-amide ligand interacting with the F-series metal is selected independent of each other non-amide ligand.

In order for the F-series metal amide to be substantially inert to further ligation, the number of ligands interacting with the F-series metal must be sufficient to satisfy the coordination number of the F-series metal or the ligands interacting with the F-series metal must be sufficiently sterically demanding to block achievement of the optimum coordination number of the F-series metal. Therefore, the key feature of the ligands interacting with the F-series metal is their collective ability to generate significant metal surface coverage to block against potential coordination by intermolecular Lewis bases.

Due to the relative ease in preparing such compounds, homoleptic F-series metal amides in which y is zero and $R_1$ and $R_2$, although independently selected relative to each other, are the same in each amide ligand interacting with the F-series metal, are preferred for use in the MOCVD method of the present invention.

Homoleptic F-series metal amides may be prepared by the metathesis reaction between a halide of the desired F-series metal and a solution of an alkali metal amide having the desired substituents attached to the nitrogen atom (i.e., —$NR_1R_2$). Due to the moisture and oxygen sensitivity of F-series metal amides, it is necessary to prepare these compounds in an inert atmosphere. Standard Schlenk or inert gas-filled glove box techniques may be employed in performing the requisite manipulations.

The alkali metal amide solution is chilled to approximately 0° C. before slowly mixing it with the F-series metal halide. The mixture is stirred and allowed to warm to ambient temperature. Once the reaction is complete, all the volatiles are removed from the product mixture at reduced pressure. The F-series metal amide product may then be purified by: (1) extracting the resulting residue with an organic solvent such as diethylether; (2) evaporating the extractant to dryness at ambient temperature and reduced pressure; (3) recrystallizing the resulting material from a mixture of approximately equal amounts of diethylether and hexanes at about –30° C. and (4) subjecting the recrystallized product to repeated fractional sublimation.

The metathesis reaction between the F-series metal halide and the alkali metal amide may be carried out using either forward or reverse addition techniques. The difference between forward and reverse addition is that in the former, aliquots of a solution containing the alkali metal amide are slowly added to the F-series element halide, while in the latter, portions of the F-series element halide are slowly added to the alkali metal amide solution. This distinction is important in that it has been discovered that the yield of F-series metal amide using the reverse addition technique is significantly greater than the yield when the forward technique is employed.

Heteroleptic F-series metal amides may be similarly prepared. For example, if x=3 and y=0, an oligomeric amido halo intermediate is first formed by reacting an F-series metal halide (e.g., $MX_3$) and one equivalent of an alkali metal amide having desired substituents bonded to the nitrogen atom (e.g., —$NR_1R_2$) using forward addition techniques. The oligomeric amido halo intermediate formed has the following empirical formula This intermediate is then reacted with one equivalent of a second alkali metal amide having desired substituents bonded to the nitrogen atom (e.g., —$NR'_1R'_2$) to form a second amido halo intermediate having the following empirical formula Preparation of the heteroleptic F-series metal amide is then completed by reacting the second amido halo intermediate with one equivalent of a third alkali metal amide having desired substituents bonded to the nitrogen atom (e.g., —$NR_1R'_2$).

In order to achieve higher purity in the heteroleptic F-series metal amide, it may be desirable to isolate the amido halo intermediates before reacting them with the alkali metal amides. Furthermore, in preparing heteroleptic F-series metal amides where $y \geq 1$, the preceding description is modified such that the first intermediate and/or subsequent intermediates, as necessary, are reacted with compounds having the desired non-amide ligand(s), Q, bonded to an alkali metal.

Listed in Table 1 are several homoleptic F-series metal amides which may be used as F-series metal source compounds in the MOCVD method of the present invention. The compounds listed in Table 1 have the general formula

TABLE 1

$$M\text{---}\left[N\begin{array}{c}R_1\\[-2pt]\diagdown\\[-2pt]R_2\end{array}\right]_3$$

| F-series Metal | $R_1$ | $R_2$ |
|---|---|---|
| Er | TMS | TMS |
| La | TMS | TMS |
| Y  | TMS | TMS |
| Pr | TMS | TMS |

An exemplary F-series metal amide in which $R_1$ and $R_2$ and the nitrogen atom to which they are attached comprise a heterocyclic ring has the structure

To prepare ZnSe or CdS semiconductor materials doped with nitrogen, the source compound for the nitrogen is a zinc amide having a vapor pressure of at least about $1\times10^{-5}$ torr at 200° C., and preferably, at least about $1\times10^{-4}$ torr at 100° C. The zinc amides have the formula wherein $R_1$, $R_2$, $R'_1$ and $R'_2$ are independently alkyl, alkenyl, aryl, or di- or trialkyl-substituted silyl, provided that if $R_1$, $R_2$, $R'_1$ and $R'_2$ are each trialkyl-substituted silyl, at least one of $R_1$, $R_2$, $R'_1$ or $R'_2$ have at least one alkyl group containing a β hydrogen. Furthermore, either one or both of the two nitrogen atoms bonded to the zinc atom along with the respective substituent groups (i.e., $R_1$, $R_2$ and $R'_1$, $R'_2$) may be part of a heterocyclic ring substituent bonded to the zinc atom. For example, the zinc amides could have the following formulas Zinc amides as defined above offer several advantages as nitrogen source compounds in MOCVD as compared to bis-bis-(trimethylsilyl) zinc amide. For example, the zinc amides of the present invention generally exhibit a more consistent vapor pressure and cleaner decomposition kinetics, are easier to purify and are stable across a wider range of MOCVD operating conditions than bis-bis-(trimethylsilyl) zinc amide.

The zinc amides, like the F-series metal amides may be homoleptic as well as heteroleptic. Similarly, the homoleptic zinc amides may be prepared by the metathesis reaction between a zinc halide and an alkali metal amide having desired substituents bonded to the nitrogen atom.

Heteroleptic zinc amides of the present invention are prepared by first forming an oligomeric amido halo intermediate by reacting a zinc halide and one equivalent of an alkali metal amide having desired substituents bonded to the nitrogen atom (e.g., —$NR_1R_2$) using forward addition techniques. The oligomeric amido halo intermediate formed has the following empirical formula $$[R_1R_2NZnX]$$

Preparation of the heteroleptic zinc amide is then completed by reacting the intermediate with one equivalent of an alkali metal amide having desired substituents bonded to the nitrogen atom (i.e., —$NR'_1R'_2$). In order to achieve higher purity in the heteroleptic zinc amide product, it may be desirable to isolate the amido halo intermediate before reacting it with the second alkali metal amide.

Listed in Table 2 are a number of zinc amides, both homoleptic and heteroleptic, which may be used as nitrogen source compounds in the MOCVD method of the present invention to incorporate nitrogen as a p-type dopant into ZnSe or CdS semiconductor material. The compounds listed in Table 2 have the following general formula

TABLE 2

$$R_1\diagdown \diagup R'_1$$
$$N-Zn-N$$
$$R_2\diagup \diagdown R'_2$$

| $R_1$ | $R_2$ | $R'_1$ | $R'_2$ | vapor pressure torr/°C. |
|---|---|---|---|---|
| TMS | iPr | TMS | iPr | 0.06/54 |
| TMS | tBu | TMS | tBu | 0.2/80 |
| TMS | TMS | TMS | tBu | 0.1/63 |
| TMS | TMS | TMS | iPr | 0.1/105 |
| TMS | Ph | TMS | Ph | 0.25/194 |
| TMS | TMS | TMS | Ph | 0.06/85 |
| DMS | iPr | DMS | iPr | 0.1/>200 |
| TMS | nPr | TMS | nPr | 0.02/123 |
| TMS | Cyhex | TMS | Cyhex | — |
| Cyhex | Cyhex | Cyhex | Cyhex | 0.17/99 |
| iPr | iPr | iPr | iPr | — |

In accordance with well-known CVD techniques, an epitaxial layer of an F-series metal can be deposited onto a substrate using the F-series metal amide source compounds of the present invention. Particularly, semiconductor materials doped with an F-series metal can be prepared by first depositing an epitaxial layer of the F-series metal onto a semiconductor substrate and then subjecting the coated substrate to rapid thermal annealing (RTA) so that the dopant diffuses into the semiconductor material. However, the RTA technique may only be employed in preparing F-series metal-doped semiconductors if the semiconductor substrate is stable at the annealing temperature. Furthermore, both F-series metal and nitrogen doped semiconductor materials can be prepared by codepositing the main elements of the semiconductor material and the desired dopant as an epitaxial layer onto a substrate. With regard to preparing nitrogen-doped ZnSe or CdS, the RTA technique is not feasible in that nitrogen can not be deposited apart from the semiconductor lattice.

Whether used to deposit an epitaxial layer of an F-series metal or to prepare a doped semiconductor material, the MOCVD methods of the present invention comprise introducing a reactant gas which comprises an F-series metal amide or zinc amide into a heated reactor chamber of an epitaxial reactor system. Epitaxial reactor systems generally comprise vessels which both store the source compounds of the materials to be deposited and provide a contact zone between a carrier gas such as hydrogen or argon and the source compounds to produce the reactant gas. Depending on whether the source compound is liquid or solid at operating conditions, this vessel is a bubbler or a percolator, respectively.

A reactant gas is produced by flowing the carrier gas through transfer lines into a storage vessel and contacting the stored source compound with the carrier gas such that some of the source compound is transferred to the vapor phase either at or below the saturation point. The temperature of the carrier gas is approximately 20° to 200° C. The flow rate of the carrier gas is in the range of about 20 standard cubic centimeters per minute (sccm) to 5 standard liters per minute. When the F-series metal amide is a dopant source, the mole fraction of the source compound in the reactant gas is about $1 \times 10^{31\ 2}$ to $10^{-8}$, preferably $10^{-6}$ to $10^{-8}$. When the metal amide is the primary element source, the mole fraction is about $10^{-1}$ to about $10^{-5}$, preferably about $10^{-2}$ to about $10^{-4}$.

The reactant gas containing the metal amide source compound then flows through a manifold and into the heated reactor chamber containing a heated substrate. The substrate preferably is preheated by rf induction heating, radiant heat, or other means known in the art to a temperature in the range of 200°–1000° C., more preferably 400°–600° C. before the reactant gas is introduced to the reactor. For photoassisted or photocontrolled decomposition of the metal amide source compounds, lesser substrate growth temperatures may be employed. The pressure in the reactor will generally be greater than about 1 torr and less than 1 atmosphere and is preferably greater than about 5 torr and less than about 0.2 atmosphere.

Generally, in preparing semiconductor materials doped with an F-series metal or nitrogen by codepositing the semiconductor material and the dopant, the relative flowrate of the dopant source compound entering the reactor chamber is controlled such that a level of doping between about $1 \times 10^{12}$ and $6 \times 10^{21}$ atoms/cm$^3$ is achieved. Similarly, if RTA techniques are employed, the dopant layer is thick enough so that upon annealing sufficient doping is attained.

When using the method of the present invention to deposit an F-series metal, highly reducing conditions are maintained in the reactor chamber. Such conditions may be maintained by providing the reactor chamber with an atmosphere of hydrogen, hydrazine, phosphine, silane or a mixture of hydrogen and an inert such as helium or argon. By contrast, when preparing ZnSe or CdS semiconductor materials doped with nitrogen, the conditions in the reactor chamber are generally not highly reducing. These conditions may be maintained by providing the reactor chamber with an atmosphere of dry air or an inert gas such as helium, argon or nitrogen. If air is used, the water content should be less than about 3% by weight and preferably, is between about 1 and about 10 ppb.

Suitable reactors for use in conducting the MOCVD methods of the present invention include those available from Spire Corporation, (Bedford, Mass.). Other reactors which are suitable for use in the MOCVD method of the present invention are described by G. E. Stringfellow in "Organometallic Vapor Phase Epitaxy: Theory and Practice" Academic Press (1989). Other parameters which influence the chemical vapor deposition (e.g., reactor geometry) are described in the Stringfellow reference and are known by those of ordinary skill in the art.

The present invention is illustrated by the following examples which are merely for the purpose of illustration and are not to be regarded as limiting the scope of the invention or manner in which it may be practiced.

EXAMPLE 1

Preparation and Purification of Er{N[Si(CH$_3$)$_3$]$_2$}$_3$

In this example, tris-bis(trimethylsilyl) erbium amide (Er{N[Si(CH$_3$)$_3$]$_2$}$_3$, MW 648.42, pink powder, mp 162° C.), a homoleptic F-series metal amide of the present invention was prepared by the metathesis reaction between bis-trimethylsilyl lithium amide (LiN[Si(CH$_3$)$_3$]$_2$) and erbium trichloride (ErCl$_3$) employing reverse addition techniques. All manipulations were performed under an atmosphere of dry nitrogen or argon using standard Schlenk or inert gas-filled glove box techniques.

The lithium amide reagent was prepared in a 500 ml three-necked, round-bottomed glass flask. The flask was equipped with a reflux condenser, a pressure-equalizing delivery funnel, an internal magnetic stirring bar, a mercury bubbler, and a nitrogen gas inlet. A solution of 20 g of hexamethyldisilazane (HN[Si(CH$_3$)$_3$]$_2$, 0.124 mole, 26.14 ml, Aldrich, 98%, used as received) in 300 ml of tetrahydrofuran (Fisher, HPLC grade, freshly distilled from sodium/benzophenone) was added to the flask and cooled to −78° C. To this solution was added 64.6 ml of a freshly titrated n-butyl lithium/hexanes solution (1.92 mole/l, Aldrich) by dropwise addition. After slow warming to ambient temperature over a period of 1 hour, the clear, slightly yellow solution of the lithium amide was stirred for 2 hours at ambient temperature and then refluxed for an additional 2 hours.

The lithium amide solution was then cooled to 0° C. and 11.0 g of anhydrous erbium trichloride ($ErCl_3$, anhydrous, 40.2 mmole, Strem Chemicals, used as received) was added in approximately 1 g portions over a period of 2 hours. The erbium halide dissolved and the solution developed a pink color. After warming on its own to ambient temperature, the solution was stirred for 24 hours at ambient temperature. A white precipitate was formed. All volatiles were removed at ambient temperature and $1 \times 10^{-2}$ torr and the resulting residue was extracted three times with 100 ml portions of diethylether (Fisher, reagent grade, anhydrous, freshly distilled from $LiAlH_4$). The combined extracts were evaporated to dryness at ambient temperature and $1 \times 10^{-2}$ torr to yield about 20 g of a pink colored powder, which was recrystallized from about 50 ml diethylether/hexanes (1/1) at −30° C.

This powder contained the lithium amide as the principal volatile impurity. The white lithium amide was sublimed at $5 \times 10^{-2}$ torr and 80° C. to a cold finger (−78° C.). The sublimation was repeated until no more lithium amide sublimed to the cold finger. The pink residue was then sublimed at $1 \times 10^{-4}$ torr and 130°–140° C. yielding 5 g (20% yield based on $ErCl_3$) of the erbium amide product in the form of a pink amorphous powder.

EXAMPLE 2

Preparation and Purification of $[Si(CH_3)_3(tBu)]NZnN[Si(CH_3)_3]_2$

In this example, $[Si(CH_3)_3(tBu)]NZnN[Si(CH_3)_3]_2$, a heteroleptic zinc amide of the present invention, was prepared by reacting zinc dichloride with hexamethyldisilamidolithium and tButrimethylsilyl lithium amide.

Hexamethyldisilamidolithium ($LiN[Si(CH_3)_3]_2$) was prepared in a 500 ml, three-necked, round-bottomed flask equipped with a reflux condenser, a pressure-equalizing delivery funnel, a magnetic stirring bar, a silicon oil bubbler and a nitrogen gas inlet. To the flask was added a solution of 20 g of hexamethyldisilazane ($HN[Si(CH_3)_3]_2$, 0.124 mole, 26.14 ml) in 200 ml of ether. The solution was cooled to 0° C. and 34.4 ml of a freshly titrated nBuLi/hexanes solution (3.6M) was added over a period of 15 minutes. At the end of the reaction, a white crystalline solid began to precipitate. After warming to ambient temperature, while stirring, the entire solution was refluxed for an additional 2 hours, then cooled to ambient temperature. Most of the solvent was removed at reduced pressure. The snow-white solid was washed five times with ether and dried under vacuum to give a quantitive yield.

tButrimethylsilylamine ($HN[Si(CH_3)_3]^tBu$) was prepared in a 500 ml Schlenk flask equipped with a magnetic stirring bar and a silicon oil bubbler. To the flask was added a solution of 25 g tertbutylamine ($tBuNH_2$, 0.341 mole) in 350 ml of ether. The solution was cooled to 0° C. and 18.52 g of trimethylchlorosilane ($ClSi(CH_3)_3$, 0.1705 mole, 21.58 ml) was added very slowly through a syringe. After warming to ambient temperature, the white solid (tBuamine hydrochloride) was removed by Schlenk filtration. The remaining clear solution was distilled at ambient temperature to yield the desired product at 118° C. Yield: 13.5 g (54%).

tButrimethylsilyl lithium amide ($LiN[Si(CH_3)_3][tBu]$) was prepared in a 250 ml Schlenk flask equipped with a magnetic stirring bar and a silicon oil bubbler. To the flask was added a solution of 13.5 g of tbutrimethylsilylamine in 100 ml of ether. The solution was cooled to 0° C. and 25.8 ml of a freshly titrated nBuLi/hexanes solution (3.6M) was added over a period of 10 minutes. After warming on its own to ambient temperature, the pale yellow, cloudy solution was refluxed for one hour, then cooled to ambient temperature. The white lithium amide was then purified by recrystallization from an ether/hexane solution.

The desired heteroleptic zinc amide was then prepared in a 1000 ml, three-necked, round-bottomed flask, equipped with two pressure-equalizing delivery funnels, a magnetic stirring bar, a silicon oil bubbler and a nitrogen gas inlet. To the flask was added a solution of 5.85 g of anhydrous zinc-chloride ($ZnCl_2$, 42.92 mmole) in 300 ml ether. After cooling the solution to −78° C., a solution of one equivalent (7.18 g, 42.92 mmole) of hexamethyldisilamidolithium in 400 ml ether was added very slowly with rapid stirring over a period of 36 hours. This mixture was then warmed to ambient temperature over a period of 10 hours and stirred for another 24 hours at this temperature. To this mixture was added one equivalent (6.49 g, 42.92 mmole) of tButrimethylsilyl lithium amide in 200 ml ether at 0° C. This addition took a period of 4 hours. After stirring overnight at ambient temperature, lithium chloride was separated by Schlenk filtration and the solvent was removed under reduced pressure. The residue was then distilled under vacuum yielding a colorless, viscous liquid at 63° C. and 0.1 Torr which solidifies at 11°–12° C.

EXAMPLE 3

MOCVD Using $Er\{N[Si(CH_3)_3]_2\}_3$ and $Er(C_5H_5)_3$

An epitaxial layer of erbium was deposited using the MOCVD method of the present invention. The tris bis (trimethylsilyl) erbium amide ($Er\{N[Si(CH_3)_3]_2\}_3$) prepared in Example 1 was utilized as the erbium source compound. This erbium amide was compared to tricyclopentadienyl erbium ($Er(C_5H_5)_3$) for purity, decomposition kinetics and as an erbium source compound in MOCVD.

Figure 1:
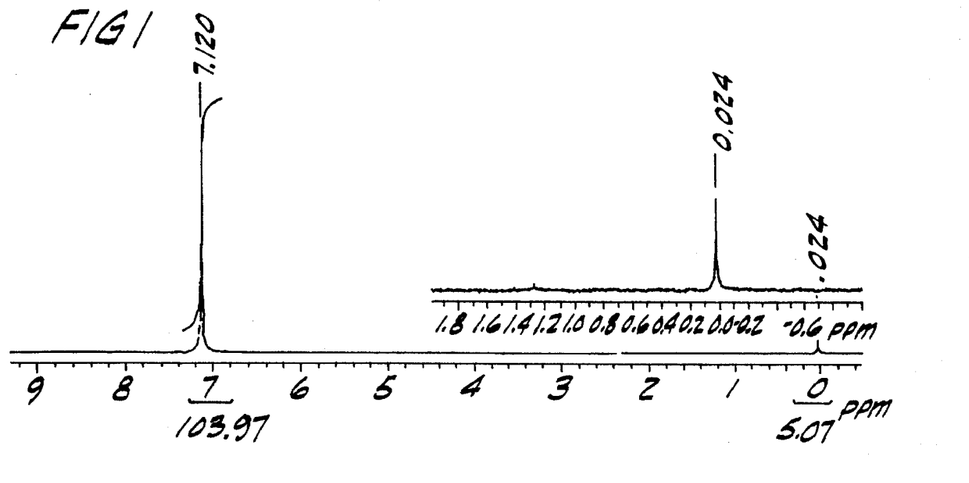
FIG. 1 is the nuclear magnetic resonance (NMR) analysis of the sample of tris-bis(trimethylsilyl) erbium amide used in Example 3 as an erbium source compound in MOCVD.

The tricyclopentadienyl erbium material was purchased from a commercial vendor and had tested impurity levels below 1 ppm. The purity of the $Er\{N[Si(CH_3)_3]_2\}_3$ utilized in this example is indicated by the NMR spectroscopy data shown in FIG. 1. The single very sharp peak implies a total contaminant concentration less than 0.1 ppm.

Figure 2:
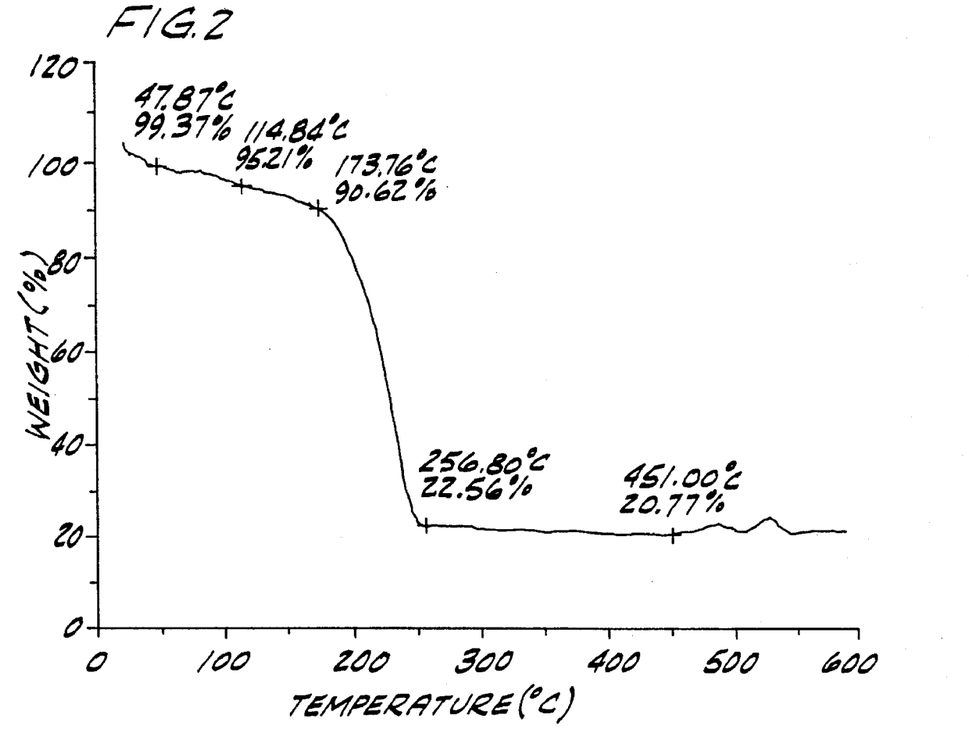
FIG. 2 is the thermal gravimetric analysis (TGA) of tris-bis(trimethylsilyl) erbium amide showing the compound's decomposition kinetics.

Decomposition kinetics of $Er\{N[Si(CH_3)_3]_2\}_3$ are shown in the thermal gravimetric analysis (TGA) in FIG. 2. The decomposition point of this material is 257° C. It sublimes rapidly at 175° C. The melting point is 162° C., and the vapor pressure at 120° C. is 0.1 torr. For comparison, the published vapor pressure of Er(C$_5$H$_5$)$_3$ is 0.01 torr at 200° C., and the melting point is 285° C.

Epitaxial layers of erbium were deposited on a silica substrate using each of the erbium source compounds. The MOCVD tests were carried out using parameters appropriate for epitaxial growth of Group IV semiconductor materials and were performed in a hydrogen atmosphere using argon as the carrier gas. The reactor pressure was maintained between 10 and 75 torr with induction heating of the susceptor to temperatures between 650° and 850° C. The erbium source compounds were stored in independent stainless steel bubblers. The bubblers were fitted with high temperature valves as were all valves used downstream from the erbium sources. The manifold carrying the erbium vapor was heated in an oven typically 10° C. above the temperature of the source to prevent condensation in the lines. The gas line from the manifold to the reactor, which contained no valves, was heated by resistance tape to the same temperature as the manifold.

Deposition of Erbium Layer Using Er(C$_5$H$_5$)$_3$

In this test, the tricyclopentadienyl erbium source compound was maintained at a temperature of 200° C. Using an argon carrier gas flow of 200 sccm diluted by 4.8 slpm of hydrogen, a layer of elemental erbium 400 nm thick was deposited in two hours at a substrate temperature of 600° C. The composition of the layer was measured by Rutherford Backscattering Spectroscopy (RBS).

Figure 3:
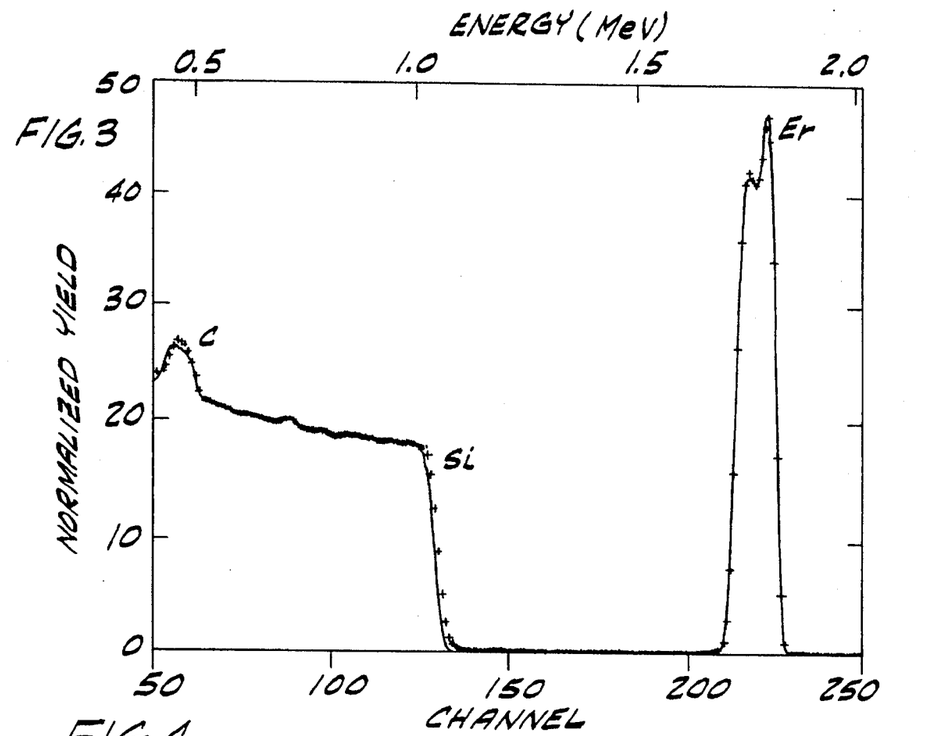
FIG. 3 is the Rutherford backscattering spectroscopy (RBS) analysis of the epitaxial layer of erbium grown on a silica substrate by MOCVD in Example 3 using tricyclopentadienyl erbium as the erbium source compound.

The RBS results for the elemental erbium layer deposited using Er(C$_5$H$_5$)$_3$ are shown in FIG. 3. Dots in FIG. 3 are measured data points while the line was fit using a multilayered model. Carbon content of this layer exceeded 90% by atomic ratio.

Deposition of Erbium Layer Using Er{N[Si(CH$_3$)$_3$]$_2$}$_3$

Figure 4:
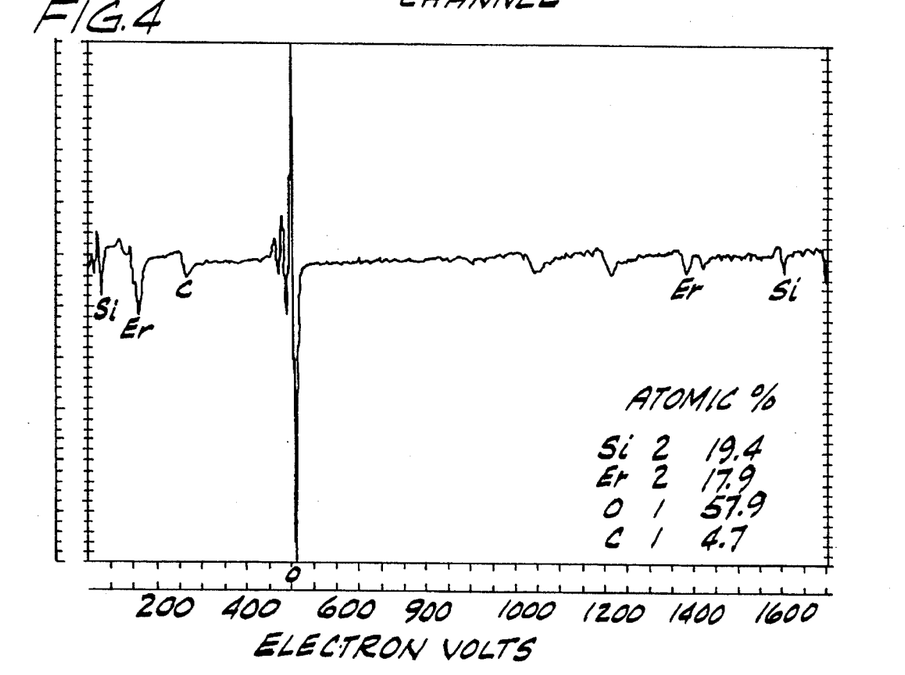
FIG. 4 is the Auger spectroscopy analysis of the epitaxial layer of erbium grown on a silica substrate by MOCVD in Example 3 using tris-bis(trimethylsilyl) erbium amide as the erbium source compound.

Initial MOCVD tests using a Er{N[Si(CH$_3$)$_3$]$_2$}$_3$ source temperature of 150° C. failed to produce any visible erbium deposits at substrate temperatures of 400° and 600° C. The Er{N[Si(CH$_3$)$_3$]$_2$}$_3$ source temperature was raised to 175° C. (see FIG. 2) and a 4 nm layer was formed on a silica coated substrate. Sputter cleaning would have removed this layer. Auger spectroscopy data for this layer is shown in FIG. 4. The carbon content observed is typical of atmospheric contamination of any sample not cleaned by sputtering. Thus, the erbium layer deposited using Er{N[Si(CH$_3$)$_3$]$_2$}$_3$ exhibited substantially decreased carbon contamination (perhaps essentially zero excluding atmospheric contamination) as compared to the erbium layer deposited using Er(C$_5$H$_5$)$_3$.

Thus, for our conditions, the erbium amide compound decomposed with little trace of silicon, nitrogen, or carbon contamination. It is therefore preferred as an erbium source compound in MOCVD.

In view of the above, it will be seen that the several objects of the invention are achieved.

As various changes could be made in the above compositions without departing from the scope of the invention, it is intended that all matter contained in the above description be interpreted as illustrative and not in a limiting sense.

What is claimed is:

1. A zinc amide having a vapor pressure of at least $1 \times 10^{-5}$ torr at 200° C., the zinc amide having the formula wherein R$_1$, R$_2$, R'$_1$ and R'$_2$ are independently isopropyl, n-propyl, cyclohexyl, alkenyl, aryl, or di- or trialkyl-substituted silyl, or together with the nitrogen atom to which they are attached comprise a heterocyclic ring, provided that if R$_1$, R$_2$, R'$_1$ and R'$_2$ are each trialkyl-substituted silyl, at least one of R$_1$, R$_2$, R'$_1$ or R'$_2$ have at least one alkyl group containing a β hydrogen.

2. A zinc amide having a vapor pressure of at least $1 \times 10^{31}$ torr at 200° C., the zinc amide having the formula wherein

R$_1$, R$_2$, R'$_1$ and R'$_2$ are independently alkyl, alkenyl, aryl, or di- or trialkyl-substituted silyl, or together with the nitrogen atom to which they are attached comprise a heterocyclic ring, provided that if R$_1$, R$_2$, R'$_1$ and R'$_2$ are each trialkyl-substituted silyl, at least one of R$_1$, R$_2$, R'$_1$ or R'$_2$ have at least one alkyl group containing a β hydrogen. R$_1$, R$_2$, R'$_1$ and R'$_2$ being selected such that the zinc amide is heteroleptic.

3. A zinc amide as set forth in claim 1 selected from the group consisting of

-continued

, and

4. An erbium amide having a vapor pressure of at least $1 \times 10^{-5}$ torr at 100° C., the erbium amide having a formula selected from the group consisting of

, wherein
Q is a monodentate or oligodentate ligand other than an amide ligand, and
x is an integer $\geq 1$, and y is an integer $\geq 0$, such that erbium is substantially inert to further ligation.

* * * * *

UNITED STATES PATENT AND TRADEMARK OFFICE
CERTIFICATE OF CORRECTION

PATENT NO. : 5,583,205
DATED : December 10, 1996
INVENTOR(S) : William S. Rees, Jr.

It is certified that error appears in the above-identified patent and that said Letters Patent is hereby corrected as shown below:

In column 9, line 62, "$1X10^{31\ 2}$" should read --$1X10^{-2}$--.

In column 14, claim 2, line 25, "$1X10^{31}$" should read --$1X10^{-5}$--;

In column 14, claim 2, line 26, "5 torr" should read --torr--.

In column 14, claim 2, line 42, "hydrogen. $R_1$," should read --hydrogen, $R_1$--.

Signed and Sealed this

Thirteenth Day of May, 1997

*Attest:*

BRUCE LEHMAN

*Attesting Officer*   *Commissioner of Patents and Trademarks*